US008642015B2

(12) United States Patent
Osbakken et al.

(10) Patent No.: US 8,642,015 B2
(45) Date of Patent: *Feb. 4, 2014

(54) TREATMENT OF ACTIVE INFECTIONS AND RELATED COMPOSITIONS

(71) Applicant: Aerosol Science Laboratories, Inc., Camarillo, CA (US)

(72) Inventors: Robert Scott Osbakken, Camarillo, CA (US); Russell N. Reitz, Camarillo, CA (US); John C. Tarrant, Camarillo, CA (US)

(73) Assignee: Aerosol Science Laboratories, Inc., Camarillo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/685,528

(22) Filed: Nov. 26, 2012

(65) Prior Publication Data

US 2013/0084251 A1    Apr. 4, 2013

Related U.S. Application Data

(63) Continuation of application No. 12/097,230, filed as application No. PCT/US2006/062170 on Dec. 15, 2006, now Pat. No. 8,337,814.

(60) Provisional application No. 60/597,660, filed on Dec. 15, 2005.

(51) Int. Cl.
*A61K 9/12* (2006.01)
(52) U.S. Cl.
USPC ............... 424/43; 128/200.14; 128/200.23
(58) Field of Classification Search
None
See application file for complete search history.

(56) References Cited

U.S. PATENT DOCUMENTS

| 6,890,907 | B2 * | 5/2005 | Speirs et al. ............... 514/38 |
| 7,531,164 | B2 * | 5/2009 | Daaka et al. ............... 424/9.1 |
| 2002/0061281 | A1 * | 5/2002 | Osbakken et al. .......... 424/43 |
| 2002/0098154 | A1 * | 7/2002 | Dyer ........................... 424/45 |
| 2004/0124185 | A1 * | 7/2004 | Patel et al. ................ 219/121.71 |
| 2009/0142277 | A1 | 6/2009 | Osbakken et al. |

OTHER PUBLICATIONS

Hans Bisgaard "Automatic Actuation of a dry powder Inhaler into a Nonelectrostatic Spacer" Am J Respir Crit Care Med vol. 157. pp. 518-521, 1998.*
Kondo, Hiroko et al., "Transitional Concentration of Antibacterial Agent to the Maxillary Sinus via a Nebulize", Acta Oto-laryngol, 1996, pp. 64-67, Suppl 525, Stockholm, Sweden.
Rogers, Duncan F., "Mucoactive Agents for Airway Mucus Hypersecretory Diseases", Respiratory Care, Sep. 2007, pp. 1176-1197, vol. 52 No. 9.

* cited by examiner

*Primary Examiner* — Michael G Hartley
*Assistant Examiner* — Nabila Ebrahim
(74) *Attorney, Agent, or Firm* — Sheppard Mullin Richter & Hampton LLP

(57) ABSTRACT

The present invention is directed to the treatment of infections and the associated symptoms of sinusitis, rhinitis and related neurological disorders of the cranial cavity and facial tissue. More specifically, the present invention is directed to aerosols that are used to treat infections and the associated symptoms of sinusitis, rhinitis and related neurological disorders of the cranial cavity and facial tissue, compositions from which the aerosols are generated and methods of generating the aerosols. In an aerosol aspect of the present invention, an aerosol for delivery to the sinus cavity of a patient is provided. The aerosol includes at least: a) one or more compounds selected from antibiotics, antifungals, leukotriene antagonists, anti-TNF compounds, antihistamines, steroidal antiinflammatories, mucolytics, estrogen, progesterone and related hormones; and, b) water. The compounds are present in the water at a concentration ranging from 0.01 mg/kg to 1000 mg/kg, and the aerosol does not contain a surfactant.

34 Claims, No Drawings

TREATMENT OF ACTIVE INFECTIONS AND RELATED COMPOSITIONS

RELATED PATENT APPLICATIONS

This application is a Continuation of U.S. application Ser. No. 12/097,230, filed Nov. 13, 2008 (now, U.S. Pat. No. 8,337,814), which is a National Stage Entry of PCT/US06/62170, filed Dec. 15, 2006, which claims the benefit of U.S. Provisional Application No. 60/597,660, filed Dec. 15, 2005, all of which are incorporated herein by reference in their entireties and for all purposes.

FIELD OF THE INVENTION

The present invention is directed to the treatment of sinusitis, rhinitis and related neurological disorders of the cranial cavity and facial tissue. More specifically, the present invention is directed to aerosols that are used to treat sinusitis, rhinitis and related neurological disorders of the cranial cavity and facial tissue, compositions from which the aerosols are generated and methods of generating the aerosols.

BACKGROUND OF THE INVENTION

U.S. Pat. No. 7,128,897 discusses pharmaceutical compositions formulated for aerosol administration to the nasal sinuses. The compositions contain one agent for treatment of sinusitis and a surfactant; they further have a surface tension between 10 dynes/cm and 70 dynes/cm.

The compositions are aerosolized using a nebulizer, such as a the Respironics Sidestream® jet nebulizer and the Pari LC® jet nebulizer. According to the patent, the resulting aerosols have a mass median aerodynamic diameter between 0.5 μm and 5.0 μm. A stated objective is to produce aerosols where less than 20% of the particles are over 5.0 μm in diameter. There is no indication within the four corners of the document, however, indicating that such a distribution was achieved.

In view of the disclosure presented in U.S. Pat. No. 7,128,897, there remains a need for aerosolization methods and related compositions that may be used to treat sinusitis, rhinitis and related neurological disorders of the cranial cavity and facial tissue.

SUMMARY OF THE INVENTION

The present invention is directed to the treatment of sinusitis, rhinitis and related neurological disorders of the cranial cavity and facial tissue. More specifically, the present invention is directed to aerosols that are used to treat sinusitis, rhinitis and related neurological disorders of the cranial cavity and facial tissue, compositions from which the aerosols are generated and methods of generating the aerosols.

In an aerosol aspect of the present invention, an aerosol for delivery to the sinus cavity of a patient is provided. The aerosol includes at least: a) one or more compounds selected from antibiotics, antifungals, leukotriene antagonists, anti-TNF compounds, antihistamines, anti-inflammatories, mucolytics; estrogen, progesterone and their related hormones; and, b) solvent. The compounds are present in the solvent at a concentration ranging from 0.01 mg/ml to 1000 mg/ml, and the liquid does not require a surfactant or other additive to aerosolize optimally.

In another aerosol aspect of the present invention, an aerosol for delivery to the sinus cavity of a patient is provided. The aerosol includes at least: a) one or more compounds selected from antibiotics, anti-fungals, leukotriene antagonists, anti-TNF compounds, antihistamines, anti-inflammatories, mucolytics; estrogen, progesterone and their related hormones; and, b) a solvent. The compounds are present in the solvent at a concentration ranging from 0.01 mg/ml to 1000 mg/ml, and the aerosol does not require a surfactant or other additive to aerosolize optimally. The aerosol is made using a method having at least the following steps: a) placing an aqueous composition comprising one or more compounds selected from a group consisting of antibiotics, antifungals, leukotriene antagonists, anti-TNF compounds, antihistamines, steroidal antiinflammatories, mucolytics; estrogen, progesterone and their related hormones into a medication reservoir of a nasal filtration aerosolizing device; and, b) forcing the composition through pores of the filter.

In a method of treatment aspect, methods of treating sinusitis, rhinitis and related neurological disorders of the cranial cavity and facial tissue are provided. The methods involve administration of the aerosols listed previously to a patient.

DETAILED DESCRIPTION OF THE INVENTION

The present invention is directed to the treatment of sinusitis, rhinitis and related neurological disorders of the cranial cavity and facial tissue. More specifically, the present invention is directed to aerosols that are used to treat sinusitis, rhinitis and related neurological disorders of the cranial cavity and facial tissue, compositions from which the aerosols are generated and methods of generating the aerosols.

Compositions used to generate the aerosols of the present invention typically include one or more compounds selected from the following classes of compounds: antibiotics, antifungals, leukotriene antagonists, anti-TNF compounds, antihistamines, antiinflammatories, mucolytics; estrogen, progesterone and their related hormones. The compositions further typically include a solvent, such as water. The concentration of compounds in the solvent usually ranges from 0.01 mg/ml to 1000 mg/ml, depending on the appropriate dose of the compound. The compositions do not require a surfactant or other additive to aerosolize optimally. Furthermore, the compositions may have an osmolality either within or outside of the range of 200 mOsm/kg to 880 mOsm/kg.

Nonlimiting examples of antibiotics include the following compound classes: cephalosporins ($1^{st}$-$4^{th}$ generation), penicillins, aminoglycosides, quinolones, tetracyclines, and macrolides. Nonlimiting examples of antivirals are oseltamivir, acyclovir, and rimantadine. Nonlimiting examples of anti-fungals are Amphotericin B, fluconazole, Itraconazole, and all forms of liposomal amphotericin. Nonlimiting examples of leukotriene antagonists are montelukast, and zafirlukast. Nonlimiting examples of anti-TNF compounds are infliximab, etanercept, and adalimumab. A nonlimiting examples of an antihistamine is azelastin. Nonlimiting examples of steroidal anti-inflammatories are budesonide, betamethasone, and mometasone. Nonlimiting examples of mucolytics are acetylcysteine, dornase alpha and saline solution. Nonlimiting examples of estrogen, progesterone and their compounds, natural or synthetic, include estradiol, estriol and estrone; and progesterone manufactured from soy or yam.

Aerosols are typically generated from compositions of the present invention using a nasal filtration aerosoling device including the following: 1) A filter with consistent 1 μm to 6 μm holes or pores. The pores are spaced relatively evenly across the filter at 15 to 150 μm between centers. The filter turns liquid medications forced through it into an aerosol. It may or may not be attached to a motor, which would vibrate the filter to increase flow through the filter. 2) A medication reservoir holding from 0.5 mL to 10 mL of the composition of the present invention. In an optimal configuration, the reservoir is sealed and pressurized to enhance liquid flow through the filter after filling. 3) A small pump or mechanical piston to pressurize the medication reservoir to between 30 and 300 psi. 4) An electronic device that creates A/C current at between 25 k and 30 k hertz to connect to electromagnets and that would vibrate the filter. 5) An aerosol reservoir to hold the aerosol after it has been created. The reservoir is typically at least 20 mL and not more than 200 mL in volume. 6) A nosepiece that has two openings with diameters from 0.25 inches to 0.4 inches and with the centers of the openings spaced between 0.55 inches and 0.7 inches apart.

Where a nasal filtration aerosolizing device is used, it's basic operation is as follows: A composition of the present invention (e.g., 1 mL to 6 mL) is poured into the medication reservoir or a unit dose container of the composition is attached to the medication reservoir. A small battery operated pump generates air pressure above the composition. A mechanical valve is turned on to allow the pressurized composition to come in contact with the filter. The same mechanism that opens the valve starts the filter vibrating. Liquid is forced through the filter and the resulting aerosol fills the aerosol reservoir. A patient holds the device with the holes in the nosepiece between ¼ inch and 1 inch below his nostrils. A one-way air valve at the opposite end of the aerosol reservoir from the inhalation holes allows air to come into the aerosol reservoir as the patient inhales. The resulting aerosol enters the patient's nasal cavities and a percentage disperses into the sinuses.

The aerosols of the present invention are characterized by their controllable size range. The mass median aerodynamic diameter (MMAD) of the aerosols ranges from 1.0 µm to 5.5 µm. It typically ranges from 2.0 µm to 5.0 µm. In certain cases, the MMAD ranges from 2.5 µm to 3.5 µm or 2.7 µm to 3.3 µm.

Moreover, 85% of the particles usually have an aerodynamic diameter ranging from 1.0 µm to 4.5 µm. Typically, 85% of particles have an aerodynamic diameter ranging from 1.5 µm to 3.5 µm.

Aerosols, as do the compositions from which the aerosols arise, typically include one or more compounds selected from the following classes of compounds: antibiotics, antifungals, leukotriene antagonists, anti-TNF compounds, antihistamines, steroidal antiinflammatories, mucolytics; estrogen, progesterone and their related hormones. The following are nonlimiting examples where more than one compound is included: one antibiotic and one antifungal; one antibiotic and one leukotriene antagonist; one antibiotic and one anti-TNF compound; one antibiotic and one antihistamine; one antibiotic and one steroidal antiinflammatory; one antibiotic and one mucolytic. The aerosols do not contain a surfactant.

Compounds contained in the aerosols are not substantially degraded by the aerosolization process. For instance, the compounds are typically at least 97% pure, are oftentimes at least 98% pure and are at least 99% pure is some cases.

The time of a single administration of an aerosol of the present invention typically varies from 1 minute to 8 minutes in length, depending on the composition used in the aerosolization device. Oftentimes, treatment involves from one to three aerosol administrations per day and, in most cases, the duration of treatment is 7 to 30 days, and often ongoing for prophylaxis. Aerosols of the present invention are used to treat a variety of different infections and resulting symptoms. Aerosols including one or more antibiotics are used to treat sinus infections; aerosols including one or more antiinflammatories are used to reduce the incidence of sinus infections, polyps, allergic symptoms and headaches; aerosols including one or more antifungals are used to treat fungal infections, which are thought to cause an increased incidence of sinus infections, polyps, allergic rhinitis and headaches; aerosols including one or more antivirals are used to alleviate symptoms of various strains of flu and colds, which often lead to bacterial sinus infections; aerosols containing one or more mucolytics are used to reduce the incidence of sinus infections by liquefying crusted mucous and promoting mucous production in patients with dry sinus cavities; and aerosols containing estrogen, progesterone or their related hormones are used to thicken epithelial tissue within the sinuses preventing infection.

The invention claimed is:

1. A method of delivering a medication aerosol to the sinus cavity of a patient, comprising preparing a medication aerosol by passing a liquid composition through a filter, and administering the medication aerosol to a patient, wherein:
the filter comprises pores;
the medication aerosol and the liquid composition do not contain a surfactant; and
the liquid composition comprises one or more anti-infective agents.

2. The method of claim 1, wherein said one or more anti-infective agents comprise an antibiotic or an antiviral.

3. The method of claim 2, wherein said one or more anti-infective agents comprise an antibiotic selected from the group of antibiotic classes consisting of cephalosporins, penicillins, aminoglycosides, quinolones, tetracyclines and macrolides.

4. The method of claim 2, wherein said one or more anti-infective agents comprise an antiviral selected from the group consisting of oseltamivir, acyclovir and rimantadine.

5. The method of claim 1, wherein said one or more anti-infective agents comprise an antifungal selected from the group consisting of amphotericin B, fluconazole, itraconazole and liposomal amphotericin.

6. The method of claim 1, wherein the filter pores range in size from 1 µm to 6 µm.

7. The method of claim 6, wherein the filter pores are a consistent size within the range from 1 µm to 6 µm.

8. The method of claim 6, wherein the filter pores are placed such that the distance between filter pore centers ranges from 15 µm to 150 µm.

9. The method of claim 1, wherein said liquid composition further comprises one or more selected from the group consisting of a leukotriene antagonist, an antihistamine, a steroidal anti-inflammatory, a mucolytic, an anti-TNF compound, estrogen, and progesterone.

10. The method of claim 1, wherein said liquid composition further comprises a leukotriene antagonist selected from the group consisting of montelukast and zafirlukast.

11. The method of claim 1, wherein said liquid composition further comprises azelastin.

12. The method of claim 1, wherein the liquid composition further comprises a steroidal antiinflammatory selected from the group consisting of budesonide, betamethasone and mometasone.

13. The method of claim 1, wherein the liquid composition further comprises a mucolytic selected from the group consisting of acetylcysteine and dornase alpha.

14. The method of claim 1, wherein the liquid composition further comprises an anti-TNF compound selected from the group consisting of infliximab, etanercept, adalimumab.

15. The method of claim 1, wherein a pressure is applied to the liquid composition to pass the liquid composition through the filter.

16. The method of claim 15, wherein the applied pressure is between 30 psi and 300 psi.

17. The method of claim 15, wherein the applied pressure is generated by a pump or by a mechanical piston.

18. A medication aerosol comprising an anti-infective agent for delivery to the sinus cavity of a patient, prepared by passing a liquid composition comprising an anti-infective agent through a filter comprising pores, thereby forming the aerosol, wherein the medication aerosol comprises an anti-infective agent and water, with the anti-infective agent present in the water at a concentration ranging from 0.01 mg/ml to 1000 mg/ml; and wherein the liquid composition and medication aerosol do not contain a surfactant.

19. The medication aerosol of claim 18, wherein said one or more anti-infective agents comprise an antibiotic or an antiviral.

20. The medication aerosol of claim 19, wherein the antibiotic is selected from the group of antibiotic classes consisting of cephalosporins, penicillins, aminoglycosides, quinolones, tetracyclines and macrolides.

21. The medication aerosol of claim 19, wherein the antiviral is selected from the group consisting of oseltamivir, acyclovir and rimantadine.

22. The medication aerosol of claim 19, wherein said one or more anti-infective agents comprise an antifungal selected from the group consisting of amphotericin B, fluconazole, itraconazole and liposomal amphotericin.

23. The medication aerosol of claim 18, wherein the filter pores range in size from 1 µm to 6 µm.

24. The medication aerosol of claim 23, wherein the filter pores are a consistent size within the range from 1 µm to 6 µm.

25. The medication aerosol of claim 23, wherein the filter pores are placed such that the distance between filter pore centers ranges from 15 µm to 150 µm.

26. The medication aerosol of claim 18, wherein said liquid composition further comprises one or more selected from the group consisting of a leukotriene antagonist, an antihistamine, a steroidal anti-inflammatory, a mucolytic, an anti-TNF compound, estrogen, and progesterone.

27. The medication aerosol of claim 18, wherein said liquid composition further comprises a leukotriene antagonist selected from the group consisting of montelukast and zafirlukast.

28. The medication aerosol of claim 18, wherein said liquid composition further comprises azelastin.

29. The medication aerosol of claim 18, wherein said liquid composition further comprises an anti-TNF compound selected from the group consisting of infliximab, etanercept, adalimumab.

30. The medication aerosol of claim 18, wherein said liquid composition further comprises a steroidal antiinflammatory selected from the group consisting of budesonide, betamethasone and mometasone.

31. The medication aerosol of claim 18, wherein said liquid composition further comprises a mucolytic selected from the group consisting of acetylcysteine and dornase alpha.

32. The medication aerosol of claim 18, wherein a pressure is applied to the liquid composition to pass the liquid composition through the filter.

33. The medication aerosol of claim 32, wherein the applied pressure is between 30 psi and 300 psi.

34. The medication aerosol of claim 32, wherein the applied pressure is generated by a pump or by a mechanical piston.

* * * * *